United States Patent [19]

Herrick et al.

[11] Patent Number: 5,049,142
[45] Date of Patent: Sep. 17, 1991

[54] INTRACANALICULAR IMPLANT FOR HORIZONTAL CANALICULAR BLOCKADE TREATMENT OF THE EYE

[76] Inventors: Robert S. Herrick, 4134 N. Rosemead Blvd., Rosemead, Calif. 90004; William F. Sardi, 1613 Chelsea Road, Ste. 251, San Marino, Calif. 91108

[21] Appl. No.: 227,528

[22] Filed: Aug. 2, 1988

Related U.S. Application Data

[60] Continuation of Ser. No. 929,895, Nov. 13, 1986, which is a division of Ser. No. 669252, Nov. 7, 1984, Pat. No. 4,660,546.

[51] Int. Cl.$^5$ .............................................. A61M 35/00
[52] U.S. Cl. ................................. 604/294; 604/891.1; 604/892.1; 604/11
[58] Field of Search .................... 604/890.1, 892.1, 11, 604/893, 294, 298; 606/167

[56] References Cited

U.S. PATENT DOCUMENTS 4,461,295 7/1984 Herrick ............................ 128/303.1

OTHER PUBLICATIONS

Wallace S. Foulds, "Intra-Canalicular Gelatin Implants in the Treatment of Kerato-Conjunctivitis Sicca", British Journal Ophthalmology (1961) 45, pp. 625–627.
Louis A. Wilson, M.D., "External Diseases of the Eye", Harper & Row, 1979, p. 150.
Symposium on Medical and Surgical Diseases of the Cornea, Transactions of the New Orleans Academy of Opthalmology.
C. V. Mosby Co. Publisher, 1980, p. 43 "Diagnosis and Treatment of Keratoconjunctivitis Sicca".
James T. Patten, M.D. "Punctal Occlusion with N-Butyl Cyanocrylate Tissue Adhesive", Opthalmic Surgery, Summer 1976, vol. 7, No. 1, pp. 24–26.
Jerre M. Freeman, M.D.; "The Punctum Plug: Evaluation of a New Treatment for the Dry Eye"; Transcripts of the American Academy of Opthalomology and Optometry; vol. 79, Nov.-Dec. 1975; pp. OP-874 through OP-879.
Jones LT.; Marquis MM, Vincent NJ: Lacrimal Function American Journal Ophthalmol 73: 658–659; 1972.

Primary Examiner—Stephen C. Pellegrino
Assistant Examiner—Robin R. Long

[57] ABSTRACT

An implant and method for treating external human eye conditions due to a deficiency of tears. The method includes the temporary blockade of the canaliculus of a patient without resorting to a surgical stitch, observing the response of the patient's eye to the temporary blockade and, if an improvement is observed, placing an implant within the horizontal portion of at least one of the canaliculi of the patient's eye. The temporary blockade may be produced by the placement of a piece of catgut in the canaliculus. The implant is constructed of a material that is nonabsorbable by the human body and is constructed to facilitate placement into and removal from the canaliculus.

23 Claims, 1 Drawing Sheet

INTRACANALICULAR IMPLANT FOR HORIZONTAL CANALICULAR BLOCKADE TREATMENT OF THE EYE

This is a continuation of application Ser. No. 06/929,895, filed Nov. 13, 1986, which is a Division of application Ser. No. 06/669,252 filed Nov. 7, 1984, and which issued as U.S. Pat. No. 4,660,546 on Apr. 28, 1987.

FIELD OF INVENTION

This invention relates to methods for treatment of the human eye having a deficiency of tears and an implant for the eye canaliculus.

RELATED INVENTIONS

This invention is an improvement over the laser punctal occlusion method disclosed and claimed in the Herrick U.S. Pat. No. 4,461,295, granted on July 24, 1984.

BACKGROUND OF INVENTION

We have discovered that certain eye problems are related to the volume of tears on the surface of the eyes. Some of these problems include dry eyes, corneal ulcer, conjunctivitis, blepharitis, contact lens problems and many other external eye diseases. Punctal occlusion has also been proven to be an effective way of treating patients with conditions such as sinusitis, hay fever, middle eye infection (chronic), post nasal drip, front headache, etc. The Herrick U.S. Pat. No. 4,461,295 discloses a method for laser punctal occlusion. The punctal occlusion technique that is the subject of the Herrick patent is a technique that has been adopted by a number of physicians across the country and which Dr. Herrick has taught them. The laser punctal technique includes the use of a temporary suture to stitch the tear drainage canals of the eyes closed to determine if a greater tear volume on the surface of the eyes would improve certain eye problems. This diagnostic procedure has come to be known as a Herrick Stitch Test and has proven to be an effective surgical technique. The stitch test is performed by anesthetizing the local area around the lower or upper punctum of the eye. Puncta are the tear drainage canals located on the upper and lower eyelids near the nose. The stitch is carefully placed by an eye surgeon utilizing magnification of the eye. If after a preselected period the eye conditions improve, then, the doctor permanently closes the punctum by using an Argon laser. The laser occlusion operation also requires local anesthesia. The punctum may be reopened at a later time if excess tearing is experienced. This reopening of the puntum is also done by surgical and laser techniques, all as disclosed in my U.S. Pat. No. 4,461,295. It has now been found that the use of a temporary stitch test and a laser punctal occlusion has certain disadvantages in that it is uncomfortable for many patients who do not want their eyes tampered with and also because of the need of having the expensive laser equipment readily available in the doctor's office. It is an expensive procedure for the patient and takes time for the doctor and the patient.

It is presently known that devices have been placed in the lacrimal system to diagnose and treat various conditions. One such device is known as the punctum plug. This is described as a silicone, polyethylene or Teflon device which is placed in the punctum with a small portion extending outside the opening so it can be removed. This punctum plug is described in an article by Jerre M. Freeman, M.D. entitled "The Punctum Plug: Evaluation of a New Treatment for the Dry Eye" and appears in the publication of the transcripts of the American Academy of Ophthalomology and Optometry, pages OP-874 through OP-879. The punctum plug disclosed in the Freeman article is a device to completely close the punctum. The Freeman punctum plug is designed to completely close the punctum opening by having a slightly larger portion projecting into the vertical portion of the canaliculus that prevents the plug from extruding or coming out and a larger smooth head at the opening that prevents the plug from passing down into the canaliculus. The head is designed to be smooth and dome-shaped to permit it to rest in the lacrimal lake and against conjunctiva and cornea with little irritation. The Freeman punctum plug is subject to being wiped out by the plug wearer.

It is also known that a Pyrex glass tube was designed by Dr. Lester Jones for placement in the canaliculus to maintain a pathway from the eye to the nose. These Jones' tubes are 10 to 18 millimeters in length with upper flanges of 3-4 millimeters. A number of other silicone and polyethylene tubes have been designed and manufactured to recanalize a stenosed canaliculus. The literature is replete with disclosures that are designed to open up the passages in the eye canals, etc., but the Freeman punctum plug is the only known device for occluding the punctum.

SUMMARY OF INVENTION

The present invention provides an improved method of performing temporary and permanent horizontal canicular blockade without resorting to local anesthesia, the Herrick stitch test, or the need for the expensive laser equipment and that is of no discomfort to the patients. The method of canalicular blockade may be simply performed in less than five minutes by a general practitioner in his office without the need for special skills or expensive equipment. The invention also is directed to a novel design for the intercanalicular implant for blockade of the punctum that may be readily inserted within the horizontal portion of the canaliculus and is also readily removable.

From a broad method standpoint, the invention comprehends a method for treating external human eye conditions due to a deficiency of tears, including the steps of temporarily blockading the canaliculus of a patient without resorting to a temporary surgical stitch, observing the response of the patient's eye to the temporary blockade after a preselected period to note any improvement in the eye condition in response to the occlusion and, if an improvement in the eye condition is noted, placing an implant within the horizontal portion of at least one of the canaliculi of the patient. The step of temporarily blockading the canaliculus comprises the placing of an absorbable (by the body), removable, element, which may be in the form of catgut, in the canaliculus. The permanent implant that may be utilized is constructed and defined of a nonabsorbable (by the body) material having an end of reduced diameter to facilitate the implantation into and removal from the canaliculus. The implant per se may be further constructed and defined to facilitate the insertion and/or the removal of the implant.

The implant for the canaliculus of the human eye is constructed of a cylindrical solid element constructed of a material that is nonabsorbable by the human body and adapted to be insertable into the canaliculus, the element has a tapered smooth end which facilitates implantation and also removal from the canaliculus.

BRIEF DESCRIPTION OF THE DRAWINGS

These and other features of the present invention may be more readily appreciated when considered in the light of the following specification and drawings, in which:

FIG. 2 is an illustration of an intercanalicular implant embodying the invention.

DETAILED DESCRIPTION OF THE INVENTION

Figure 1:
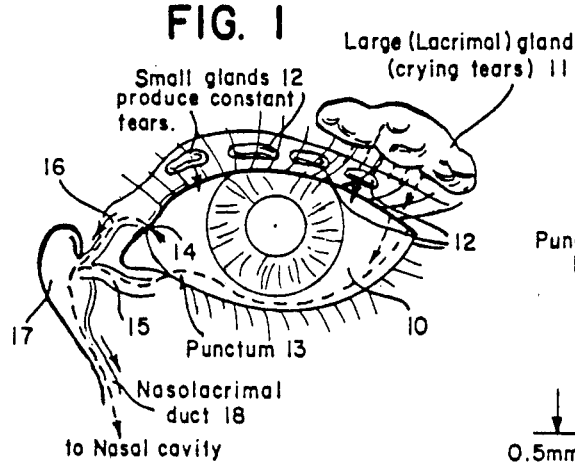
FIG. 1 is an illustration of the lacrimal system of the eye.

To facilitate the understanding of the present invention, a brief description of the human eye and the associated lacrimal system showing the paths of the tears from the sources of the tears to the nasal cavity will first be examined. The eye 10 illustrated in FIG. 1 includes the cornea and pupil as is well known. The source of the tears for the eye 10 are the crying tears which are produced by the large lacrimal gland 11, illustrated in the upper right hand portion of the drawing, and the constant tears are produced by a series of small glands 12 which are located below the large gland 11 and spaced apart above the cornea of the eye 10. The constant tears are the ones that are to be preserved in accordance with the present invention. Approximately 400 drops (9.5 milliliters) of tears are produced by the normal eye during the day and fewer tears are produced at night during sleep. Tears also protect the eye from infection since they contain an enzyme called lysozyme that acts as an antibiotic. With age, the eye produces less tears (about 60% less at age 65 than at age 18). The tears flow over the eyes and drain through small openings called puncta located in the lids of the eyes. The majority of the tears flow over the eyes and drain through the lower punctum and into the nasal passages. As illustrated in FIG. 1, the tears flow into the lower punctum 13 and upper punctum 14 which form openings into the corresponding lower canaliculus 15 and an upper canaliculus 16. In exiting the canaliculi 15 and 16, the tears merge in the lacrimal sac 17 from where they travel to the nasal lacrimal duct 18 and then drain to the nasal cavity (not shown). The canaliculi 15 and 16 are the drainage channels of the eyes and are about 10 millimeters long. The puncta 13 and 14 are the external openings of the surface of the eyelids that respectively lead to the canaliculi 15 and 16. The punctum is about 0.3 millimeters in diameter and is surrounded by a ring of connected tissue. From the punctal openings the canaliculi 15 and 16 run vertically for about 2 millimeters and then horizontally for about 8 millimeters. At the vertical canaliculi there is an ampula or sac which is 2 to 3 millimeters at its widest portion. This ampula narrows into the horizontal canaliculus which is only about 0.5 millimeters in diameter. The implant is to be placed in the horizontal portion of the canaliculus 15 or 16, as diagrammatically illustrated in FIG. 2, wherein the implant is identified as Imp.

Figure 2:
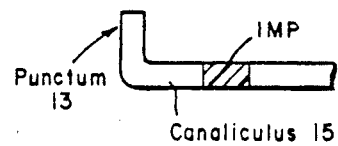
FIG. 2 is a schemmatic, enlarged view illustrating the configuration of the vertical and horizontal portion of a canaliculus from the punctum end with a removable implant formed of a collagen material, e.g. catgut, implant positioned in the horizontal portion of the canaliculus.

The present invention generally follows the two step procedure disclosed in my prior U.S. Pat. No. 4,461,295, but eliminates the need for anesthesia, the laser equipment and the aforementioned problems associated therewith. To this end, a temporary blockade of the canaliculus of the patient is provided, without resorting to a temporary surgical stitch, to observe the response of the patient to the temporary blockade and, if improvements in the eye conditions of the patient are noted, a permanent blockade of the canaliculus is utilized by placing an implant within the horizontal portion of at least one of the canaliculi of the patient. To this end, the temporary blockade of the canaliculus is performed by inserting a piece of absorbable (by the body) material, such as catgut (shown in FIG. 2), in the canaliculus of the patient. It is well known to those skilled in the art that catgut is a suture material which consists primarily of collagen, a fibrous protein, and a description thereof is set forth in the 1982 PHYSICIANS DESK REFERENCE FOR OPHTHALMOLOGY, pages 19 through 21. The catgut may be a piece of 3-0 gauge catgut of approximately 5 millimeters in length. The doctor can place the catgut in the canaliculus of the patient under magnification without anesthesia through the use of a jeweler's forceps. The piece of catgut will swell in the canaliculus after placement therein. The catgut will remain in place for up to two weeks before it dissolves. Prior to dissolution, the catgut can be removed and, if desired, can be removed the same day it is implanted. This temporary occlusion of the canaliculus by means of the catgut replaces the need for the temporary stitch or the Herrick stitch test and the associated procedures that heretofore had been thought necessary. As in my previous patent, the patient is observed to determine if the eye condition improves as a result of the occlusion of the canaliculus preventing the drainage of the tears and, if so, a permanent implant Imp is placed in the canaliculus. It is preferred that the implant Imp be placed in the horizontal portion of the canaliculus, as illustrated in FIG. 2.

Figure 3:
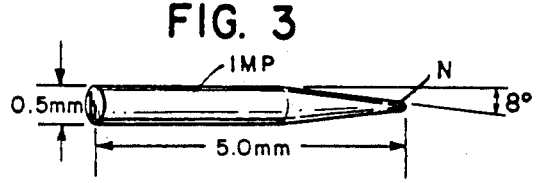

The implant Imp can be made to totally block the canaliculus or can be made with tiny passageways therethrough to permit varying amounts of tears to pass, depending upon the condition and needs of the patient as observed by the doctor. The total blockade is the usual case. The implant Imp may be constructed of materials that are nonabsorbable by the human body, such as a small piece of soft rubber or plastics, such as silicone, polyethylene, polypropelene, or Teflon having a length of approximately 5 millimeters. The implant Imp, however, may have lengths that fall within the range of 5 to 8 millimeters and diameters of 0.3 to 1.2 millimeters. The preferred diameter for the implant Imp is 0.5 millimeters. The basic configuration of the implant Imp is illustrated in FIG. 3 and is constructed and defined with one end of reduced diameter providing a smooth snub nose N and tapering from the nose N to the full diameter of 0.5 millimeters. As shown in FIGS. 3 through 10, the slope of the tapered end, referred to herein as the smooth continuously tapered end, or nose N defines a small acute angle, in the order of about 8°, relative to the cylindrical portion of the element defined by the implant Imp. The tapered end has a length which is between about one half of the axial length of the body portion and the axial length of the body portion. The narrow end of the implant Imp is placed in the punctum with forceps holding the blunter end, or the wider end, of the implant. The implant Imp is advanced through the punctum into the vertical portion of the canaliculus until it is advanced within the horizontal canaliculus, wherein it will reside. The permanent placement of the implant Imp is aided by the eye lid blink which propels fluid nasally into the canaliculus and by the negative pressure in the canaliculus. With this arrangement, the implant Imp is not easily rubbed out or washed out, as in the prior art device. The design of the implant Imp with a tapered end facilitates implantation and also removal thereof. The removal of the implant Imp is done by a doctor applying external pressure to the eye. For this purpose, the eye surgeon can utilize instruments to "massage" the canaliculus to advance it out of the punctum.

An advantage of the implant Imp relative to the laser blockade is that it may be readily and inexpensively removed to accommodate patients subject to seasonal changes and who experience dry eyes only in the summer months, so that the implant can be removed after the summer months. It can also be removed from patients who experience excess tearing (epiphora). A further advantage of the use of the implant Imp is that it prevents fast exit of medications placed on the surface of the eye, thereby rendering the medications more effective and longer lasting. The implant Imp would be contraindicated in patients who have a deformed canaliculus.

Figure 4:
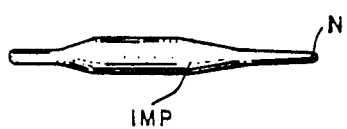
FIGS. 4 through 11 are alternate designs of intercanalicular implants for the purposes of the present invention.
Figure 5:
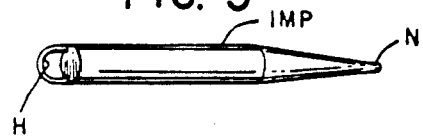
Figure 8:
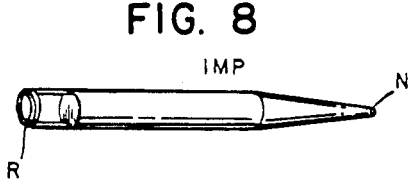

Now referring to FIG. 4 wherein an alternate design of the implant Imp for use in accordance with the present invention is illustrated. The implant of FIG. 4 has both ends defined with reduced diameters and a full diameter intermediate the ends to facilitate insertion and removal. The alternate designs illustrated in FIGS. 5 through 11 are also provided to further facilitate insertion and removal of the implants Imp. The embodiment illustrated in FIG. 5 is provided with a U-shaped handle H extending outwardly from the larger end of the implant Imp to be used for easier removal of the implant by grasping the handle H. Similarly, the implant Imp illustrated in FIG. 7 has attached thereto a thread TH that is secured to the implant at the larger end for easy removal. The thread TH may be constructed of nylon and have an adhesive patch AD secured to the free end thereof which may be applied along the nose of the patient for securing the thread TH thereto. The thread TH allows the implant Imp to be pulled through the punctum. Similarly, FIG. 8 illustrates an implant Imp that has a ring R constructed integrally with the implant and spaced outwardly a preselected distance from the end of the implant for ease of grasping of the implant for removal thereof.

Figure 6:
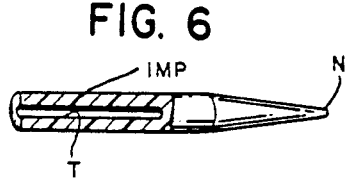
Figure 7:
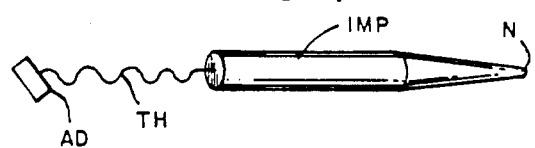
Figure 9:
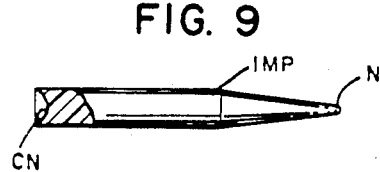
Figure 10:
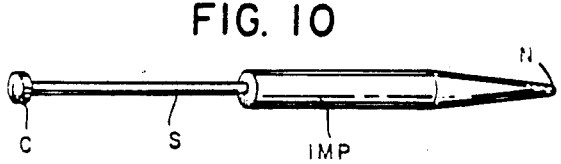

FIG. 6, 9 and 10 illustrate implants Imp that include means for facilitating the insertion of the implant into the canaliculus. FIG. 6 illustrates an implant Imp having a hollow or axial tunnel T for facilitating insertion of the implant by the use of a stylet. FIG. 10 illustrates the same implant with a stylet arranged in the tunnel T. The stylet is identified by the letter S as a longitudinally extending thin probe with a cap C at the exposed end. FIG. 9 illustrates an implant Imp that has a concave notch CN at the large end of the implant, also, utilized for aiding the insertion of the implant.

Figure 11:
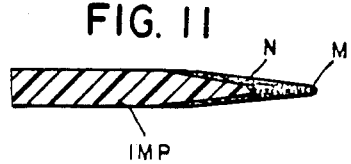

FIG. 11 illustrates an implant Imp that may be constructed of two parts, with the second part M having a preselected configuration to be mounted to the nose N of the implant Imp and for loading it with medication to be delivered to the nasal passages, the stomach, or for any systemic medication. The illustrated configuration for the part M has one end defined to be complementary to the nose end of the part Imp to be carried thereby and a blunt nose for +he opposite end. It should also be noted that the intercanalicular implant can also be used as a carrier or medium for distributing medications throughout the body. These medications can be loaded onto the intercanalicular implant Imp for timed release dosages to the eye. This release would work as a result of the reflex action of the eye and could be used, for example, to distribute antibiotics to the cornea, or glaucoma medications to the eye.

It should be noted at this point that to use a Schirmer tear strip paper placed inside the lower eyelid to determine if a patient has normal tear production is known. This Schrimer tear strip test was introduced by an Otto Schirmer in 1903 as a guide to, or confirmation of, the diagnosis of Keratitis Sicca. This test is now widely used and relied on by ophthalmologists. The base line secretions or the constant tears may be evaluated in theory by first applying a topical anesthetic to the eye to eliminate reflex lacrimation before insertion of the standard strip of filter paper. It has been found that the Schirmer tests may be misleading, although the Schirmer tests are routinely used with anesthtic and it has been found that it is only helpful when an abnormally low test result is obtained in the order of less than 3 millimeters of wetting. If as a result of the Schirmer test a dry eye is detected, then the temporary blockade of the canaliculus may be omitted and the permanent implant placed in the canaliculus immediately.

In testing for purposes of invention, the implant Imp, similar to that illustrated in FIG. 2, was constructed from a plain piece of clear silicone plastic and placed in a patient. The silicone plastic is not absorbable by the human body. However, as state hereinbefore, a temporary removable implant comprising a collagen material, e.g. catgut, is preferable for practicing this invention.

We claim:

1. An implant for insertion into the canaliculus of the human eye comprising a substantially cylindrical, solid element constructed of a material that is non-absorbable by the human body and having a selected diameter to be completely insertable into the horizontal portion of the canaliculus of the human eye without protrusion from the canaliculus to prevent the drainage of tears through the canaliculus, said element having a smooth continuously tapered end having a slope of about 8° from the cylindrical portion of the element to facilitate implantation into and removal from the canaliculus.

2. An implant for the canaliculus of the human eye as defined in claim 1 where the opposite end of said solid element from the smooth continuously tapered end has means for facilitating the removal of the element from the canaliculus.

3. An implant for the canaliculus of the human eye as defined in claim 1 or 2 wherein said element has a length of approximately 5 to 8 millimeters.

4. An implant for the canaliculus of the human eye as defined in claim 2 wherein the opposite end of said element from the smooth continuously tapered end is defined with a handle as the means for facilitating the removal of the element from the canaliculus.

5. An implant for the canaliculus of the human eye as defined in claim 2 wherein the opposite end of said element from said smooth continuously tapered end is defined with a ring spaced from the opposite end and secured thereto as the means for facilitating the removal of the element from the canaliculus.

6. An implant for the canaliculus of the human eye as defined in claim 2 wherein the opposite end of said element from said smooth continuously tapered end is defined with a thread secured to the opposite end to facilitate the removal of the element from the canaliculus.

7. An implant for the canaliculus of the human eye as defined in claim 1 wherein the opposite end of said element from the smooth continuously tapered end has means for facilitating the insertion of the element into the canaliculus.

8. An implant for the canaliculus of the human eye as defined in claim 7 wherein the opposite end of said element from said smooth continuously tapered end is defined with a concave notch for facilitating the complete insertion into the canaliculus.

9. An implant for the canaliculus of the human eye as defined in claim 7 wherein the opposite end of said element from the smooth continuously tapered end is defined with a stylet secured thereto as the means for facilitating the complete insertion into the canaliculus.

10. An implant for the canaliculus of the human eye as defined in claim 7 wherein the opposite end of said element is defined with a longitudinally extending aperture for facilitating the insertion of the element into the canaliculus.

11. An implant for the canaliculus of the human eye as defined in claim 1 wherein the smooth continuously tapered end carries a tip having a preselected medication loaded thereon for distribution to the nasal passages or to the stomach or other parts of the body.

12. An implant for the canaliculus of the human eye as defined in claim 1 wherein the element is loaded with a preselected medication for time released dosages to the eye.

13. A removable implant for insertion through the punctum and into the horizontal portion of the canaliculus of the human eye to establish an horizontal canalicular blockade comprising:
an element formed of a material that is non-absorbable by the human body having located at one end thereof a wide end which has a selected geometrical dimension capable of passing through the punctum of the eye into the canaliculus, said element having located at an opposite spaced end from said wide end in a reduced dimension smooth continuously tapered end which commences tapering at a selected location on said element to facilitate implantation into and removal from the canaliculus, said element having a preselected axial length between said wide end and the selected location; wherein the geometrical dimension of the reduced dimension of said smooth continuously tapered end at the selected location is substantially equal to that of said wide end, said smooth continuously tapered end tapering from said selected location to the end thereof over a length that is between about one half of the said axial length and said axial length.

14. The removable implant of claim 13 wherein the smooth continuously tapered end has a slope in the order of about 8° relative to the wide end.

15. The removable implant of claim 13 wherein the element has a length in the order of about 0.5 millimeters to about 0.8 millimeters, and a diameter in the order of about 0.3 millimeters to about 1.2 millimeters.

16. A removable implant for insertion through the punctum into the horizontal portion of the canaliculus of the human eye to establish a horizontal canalicular blockade comprising:
an element formed of a collagen material having located at one end thereof a first end which has a selected geometrical cross-sectional dimension defining a cylindrical shaped body portion having a smooth continuous outer surface which is capable of passing through the punctum of the eye into the canaliculus and having located at an opposite spaced end, a second end having a geometrical cross-sectional dimension which is substantially equal that of said first end to facilitate implantation into and removal from the canaliculus, said cylindrically shaped element having a preselected axial length between said first end and said second end.

17. The removable temporary implant of claim 16 wherein said collagen material is catgut.

18. The removable temporary implant of claim 16 wherein said element is formed of a fibrous protein material.

19. A removable implant for insertion through the punctum and into the horizontal portion of the canaliculus of the human eye to establish a horizontal canalicular blockade comprising:
an element formed of a material that is absorbable by the human body comprising
a cylindrically shaped body portion which has a selected geometrical dimension capable of passing through the punctum of the eye into the canaliculus; and
a smooth continuously tapered end operatively attached to one end of said cylindrically shaped body portion, said tapered end having a reduced dimension tapered surface which commences tapering where said smooth continuously tapered end is attached to said body portion to facilitate implantation into and removal from the canaliculus, said element having a preselected axial length between said body portion and the one end and said smooth continuously tapered end tapering from said body portion said smooth continuously tapered end having a length that is between about one half of the said axial length and said axial length.

20. The removable implant of claim 19 wherein said absorbable material is a catgut.

21. The removable implant of claim 19 wherein catgut is a collagen material.

22. The removable implant of claim 19 wherein said collagen material is formed of a fibrous protein material.

23. An implant for the complete insertion into the canaliculus of the human eye comprising a substantially cylindrical, solid element formed of a material that is non-absorbable by the human body having at least one single passageway extending therethrough for permitting a preselected volume of tears to drain therethrough constructed of a material that is non-absorbable by the human body and having a diameter of approximately 0.3-1.2 mm. capable of being completely insertable into the horizontal portion of the canaliculus of the human eye without protrusion from the canaliculus and discomfort to a human and yet substantially preventing the drainage of tears through the canaliculus, said element having a tapered end to facilitate implantation into and removal from the canaliculus.

* * * * *